United States Patent [19]

Lilje

[11] Patent Number: 4,540,795

[45] Date of Patent: Sep. 10, 1985

[54] FLUORONITROARALKYLOXAZOLINES, DERIVATIVES THEREOF, AND NUCLEOPHILIC SUBSTITUTION PROCESSES FOR PREPARING THEM

[75] Inventor: Kenneth C. Lilje, Baton Rouge, La.

[73] Assignee: Ethyl Corporation, Richmond, Va.

[21] Appl. No.: 469,726

[22] Filed: Feb. 25, 1983

[51] Int. Cl.³ ............................................ C07D 263/10
[52] U.S. Cl. .................................... 548/239; 560/102; 260/465 D
[58] Field of Search ........................ 548/239, 238, 237

[56] References Cited

U.S. PATENT DOCUMENTS

| 3,641,040 | 2/1972 | Carney et al. | 424/244 |
|---|---|---|---|
| 3,657,230 | 4/1972 | Carney et al. | 424/274 |
| 3,755,427 | 8/1973 | Adams et al. | 260/465 G |
| 3,767,805 | 10/1973 | Carney et al. | 424/274 |
| 3,868,391 | 2/1975 | Carney et al. | 424/274 |
| 3,901,906 | 8/1975 | Kozlik | 548/237 |
| 3,936,467 | 2/1976 | Carney et al. | 424/274 |
| 3,959,364 | 5/1976 | Armitage et al. | 562/460 |
| 3,993,763 | 11/1976 | Carney et al. | 424/274 |
| 3,997,669 | 12/1976 | Carney et al. | 424/274 |
| 4,010,274 | 3/1977 | Giraldi et al. | 424/274 |
| 4,126,691 | 11/1978 | Carney et al. | 424/274 |
| 4,163,788 | 8/1979 | Carney et al. | 424/274 |
| 4,239,901 | 12/1980 | Rainer | 424/273 P |
| 4,266,069 | 5/1981 | Walker | 260/465 D |
| 4,278,516 | 7/1981 | Zaiko et al. | 260/465 D |
| 4,324,904 | 4/1982 | Hylton et al. | 260/465 D |
| 4,370,278 | 1/1983 | Stahly et al. | 562/492 |

OTHER PUBLICATIONS

Morrison and Boyd, "Organic Chemistry", 3rd Ed., pp. 737-738, Allyn and Bacon, Inc., Boston (1973).
Burger, A., Medicinal Chemistry, 2nd Ed., p. 42, Interscience Publishers, Inc., N.Y., (1960).

*Primary Examiner*—Donald G. Daus
*Assistant Examiner*—S. A. Gibson, Sr.
*Attorney, Agent, or Firm*—Donald L. Johnson; John F. Sieberth; Patricia J. Hogan

[57] ABSTRACT

Fluoronitroaralkyloxazolines are prepared by reacting a fluoronitroaromatic compound with an alpha-substituted 2-alkyloxazoline in an inert solvent and in the presence of a base. Fluoronitroaralkyloxazolines are useful intermediates for the synthesis of pharmaceuticals, such as flurbiprofen.

3 Claims, No Drawings

FLUORONITROARALKYLOXAZOLINES, DERIVATIVES THEREOF, AND NUCLEOPHILIC SUBSTITUTION PROCESSES FOR PREPARING THEM

TECHNICAL FIELD

This invention relates to fluoronitroaralkyloxazolines and derivatives thereof—more particularly to processes for preparing the oxazolines and derivatives.

BACKGROUND

As disclosed in Japanese Patent Publication 45-29369 and in U.S. Pat. Nos. 3,755,427, 3,901,906, 3,959,364, 4,266,069, 4,278,516, and 4,324,904, there is a variety of known techniques for the preparation of flurbiprofen, i.e., 2-(2-fluoro-4-biphenylyl)propionic acid, and similar compounds having desirable anti-inflammatory, analgesic, and anti-pyretic properties. Some particularly interesting techniques are taught in U.S. Pat. No. 3,901,906 (Kozlik), which discloses that flurbiprofen and similar materials can be prepared from fluoronitroaralkyloxazolines, such as 2-[1-(2-fluoro-4-biphenylyl)ethyl]-4,4-dimethyloxazoline, which in turn may be prepared, e.g., by (1) reacting an appropriate arylmagnesium halide or aryllithium with a 2-haloalkyl-4,4-disubstituted oxazoline, (2) reacting an aryl halide with a 4,4-disubstituted oxazolinylalkyllithium or a 4,4-disubstituted oxazolinylalkylmagnesium halide, or (3) reacting an appropriate aralkanoic acid with a suitable aminoalkanol.

Unfortunately, the conventional techniques of preparing these flurbiprofen-type compounds have the disadvantage of being tedious and time-consuming. It would obviously be a welcome contribution to the art to provide a method of synthesizing the compounds, as well as intermediates therefor, in a simple, straightforward manner.

U.S. Pat. No. 4,370,278 (Stahly et al.) and copending application Ser. Nos. 452,518 (Barbara Clack Stahly et al.) and 452,617 (G. Patrick Stahly et al.) filed Dec. 23, 1982, disclose such improved syntheses wherein the intermediates are prepared by nucleophilic substitution processes utilizing nitrile and ester nucleophiles. These processes have decided advantages over the prior art but have the disadvantage of utilizing nucleophiles which tend to lead to excessive by-product formation.

STATEMENT OF INVENTION

An object of this invention is to provide novel processes for preparing fluoronitroaralkyloxazolines.

Another object is to provide such processes which permit the preparation of the oxazolines in good yield with high selectivity in a very simple and straightforward manner.

A further object is to provide novel, improved processes for preparing derivatives of fluoronitroaralkyloxazolines, e.g., flurbiprofen and the like.

These and other objects are attained by (A) reacting a fluoronitroaromatic compound with an alpha-substituted 2-alkyloxazoline in an inert solvent and in the presence of a base so as to form a fluoronitroaralkyloxazoline and (B) when appropriate, converting the fluoronitroaralkyloxazoline to a desired derivative thereof.

DETAILED DESCRIPTION

Fluoronitroaromatic compounds utilizable in the practice of the invention include a variety of such compounds—the chief requirements for their utility being that (1) they bear at least one ar-nitro and at least one ar-fluoro substituent, (2) they contain at least one replaceable hydrogen on an aromatic ring to which a nitro group and a fluoro substituent are attached, and (3) they be devoid of substituents which would interfere with the desired reaction, which appears to occur by a nucleophilic substitution mechanism.

Thus, the utilizable fluoronitroaromatic compounds include compounds having one or more simple or fused aromatic rings containing five or six members and either bearing no substituents other than the required nitro and fluoro substituents or also bearing any of a variety of inert substituents, i.e., substituents that do not interfere with the desired reaction, such as alkyl, alkoxy, alkylmercapto, trifluoromethyl, dialkylamino, dialkanoylamino, cyano, dialkylcarbamoyl, alkylsulfonyl, dialkylsulfamoyl, alkoxyalkyl, haloalkyl, cycloalkyl, halocycloalkyl, etc.—any alkyl chains in the substituents generally being lower alkyl, i.e., $C_1$–$C_6$ alkyl, chains.

When the aromatic ring bearing the required nitro and fluoro substituents is a six-membered ring, there will be at least one replaceable hydrogen in a position para or ortho to the carbon bearing the nitro substituent; and it is preferred that there be a replaceable hydrogen in the para position. Fluoronitroaromatic compounds having a five-membered ring should have a replaceable hydrogen on a carbon adjacent to, or separated by two ring atoms from, the carbon bearing the nitro substituent.

Exemplary of fluoronitroaromatic compounds they may be used in the practice of the invention are (A) heterocyclic compounds which preferably contain five- or six-membered rings having aromatic character, such as 2-fluoro-4-nitropyridine-N-oxide, 6-fluoro-5-nitroisoquinoline, 6-fluoro-5-nitroquinoline, 7-fluoro-8-nitroquinoline, 3-fluoro-2-nitrothiophene, etc., (B) fused-ring aromatic compounds, such as 4-fluoro-1-nitronaphthalene, 4-fluoro-2-nitronaphthalene, etc., (C) aromatic compounds containing a plurality of simple rings, such as 4-fluoro-2-nitrobiphenyl, 2-fluoro-3-nitrobiphenyl, 2-fluoro-4-nitrobiphenyl, 4-benzyl-2-fluoronitrobenzene, 5-fluoro-2-nitrodiphenyl ether, etc., and (D) aromatic compounds containing a single simple ring, such as the 2-, 3-, and 4-fluoronitrobenzenes, 2-fluoro-6-methylnitrobenzene, 2-ethyl-6-fluoronitrobenzene, 2,3-dimethyl-5-fluoronitrobenzene, 2,5-dimethyl-6-fluoronitrobenzene, 2,6-diethyl-3-fluoronitrobenzene, 3,4-dibutyl-6-fluoronitrobenzene, 3,5-dimethyl-2-fluoronitrobenzene, the 2,3-, 2,4-, 2,5-, 2,6-, 3,4-, and 3,5-difluoronitrobenzenes, 4-fluoro-1,2-dinitrobenzene, 5-fluoro-1,3-dinitrobenzene, 3-fluoro-2,6-dinitrotoluene, 5-fluoro-2-nitro-N,N-diethylaniline, 2-fluoro-4-nitro-N-ethylacetanilide, 5-fluoro-2-nitrobenzyl cyanide, 6-fluoro-2-nitrophenylacetate, etc.

In some cases, polynitrofluoroaromatic compounds may undergo substitution reactions whereby one of the nitro groups is replaced by the oxazoline reactant. Therefore, the possibility of this competitive reaction should be kept in mind when selecting a polynitrofluoroaromatic for use in the process.

The preferred fluoronitroaromatic compounds are mononuclear compounds, more preferably fluoronitrobenzenes, and most preferably fluoronitrobenzenes having a replaceable hydrogen in the position para to the nitro group and a fluoro substituent in the position ortho to the nitro group. A particularly preferred fluoronitroaromatic compound is 2-fluoronitrobenzene, which is readily converted in good yield with high selectivity into 2-(3-fluoro-4-nitrobenzene)alkyloxazolines, which in turn are useful intermediates for the synthesis of various pharmaceutically-active agents, such as flurbiprofen and analogs thereof.

The alpha-substituted 2-alkyloxazolines that can be used in the practice of the invention also include a variety of such compounds, which—in general—may be represented by the formula:

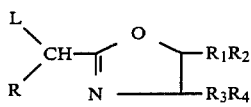

wherein L is a leaving group; R is halo (preferably chloro) or more preferably a hydrocarbyl (e.g., alkyl, alkenyl, alkynyl, cycloalkyl, cycloalkenyl, aryl, aralkyl, etc.) or hydrocarbyloxyhydrocarbyl (e.g., alkoxyalkyl, aryloxyalkyl, alkoxyaryl, alkoxycycloalkyl, etc.) group which most preferably contains up to about 10 carbons; and $R_1$, $R_2$, $R_3$, and $R_4$ are independently selected from hydrogen and hydrocarbyl groups which preferably contain not more than about 10 carbons and most preferably are alkyl groups.

Exemplary leaving groups, L, include halo, aryloxy, haloaryloxy, alkylthio, cycloalkylthio, arylthio, aralkylthio, haloalkylthio, halocycloalkylthio, haloarylthio, haloaralkylthio, or—less preferably—alkoxy, cycloalkoxy, aralkoxy, haloalkoxy, halocycloalkoxy, haloaralkoxy, and the like, as well as other suitable leaving groups which have been described in the literature, e.g., in Golinski et al., "'Vicarious' Nucleophilic Substitution of Hydrogen in Aromatic Nitro Compounds," *Tetrahedron Letters*, Vol. 37, pp. 3495–8 (1978) and in Makosza et al., "Vicarious Substitution of Hydrogen in Aromatic Nitro Compounds with Acetonitrile Derivatives," *Journal of Organic Chemistry*, Vol. 45, pp. 1534–5 (1980).

When the leaving group is an organic group, it is generally preferred that the group contain not more than about 10 carbons, although organic leaving groups having an even higher carbon content are satisfactory in the practice of the invention. Preferably, the leaving group is halo, i.e., chloro, bromo, fluoro, or iodo; and it is more preferably chloro or bromo, most preferably chloro.

Exemplary of utilizable alpha-substituted 2-alkyloxazolines are 2-(1-chloroethyl)-4,4-dimethyloxazoline, 2-(1-chloropropyl)-4,4-dimethyloxazoline, 2-(1-chlorobutyl)-4,4-dimethyloxazoline, 2-(1-chloroethyl)-4,4-diethyloxazoline, 2-(1-chloroethyl)-4-ethyl-4-methyloxazoline, 2-(1-chloroethyl-4,5-dimethyloxazoline, 2-(1-chloroethyl)-5,5-dimethyloxazoline, 2-(1-chloroethyl)oxazoline, the corresponding bromo and iodo compounds, and the like. The alpha-halo-2-alkyloxazolines in which the alkyl group contains at least two carbons are especially preferred, although similar oxazolines in which the alpha-halo substituent is replaced by one of the other leaving groups mentioned above are also highly desirable. When not commercially available, the oxazolines can be prepared, e.g., by reacting an acid chloride corresponding to the formula R—CHL—COCl with an amino alcohol corresponding to the formula $H_2N$—$CR_3R_4$—$CR_1R_2OH$ and treating the product with $SOCl_2$—L, R, $R_1$, $R_2$, $R_3$, and $R_4$ in these formulas having the same significance as in the alkyloxazoline formula given above.

The solvent used in a fluoronitroaromatic compound/oxazoline reaction of the invention may be any solvent that is inert under the conditions of the reaction, i.e., any solvent that will not prevent the reaction from occurring. Such solvents are substantially anhydrous and are generally aprotic, although solvents such as liquid ammonia are also utilizable.

Illustrative aprotic solvents which may be employed in the process of the invention include ethers such as diethyl ether, dibutyl ether, 1-ethoxyhexane, tetrahydrofuran, 1,4-dioxane, 1,3-dioxolane, diglyme, 1,2-diethoxyethane, anisole, etc.; tertiary amines such as pyridine, N-ethylpiperidine, triethyl amine, tributyl amine, N,N-diphenyl-N-methyl amine, N,N-dimethylaniline, etc.; and other aprotic solvents. However, the preferred aprotic solvents are dipolar aprotic solvents such as dimethyl sulfoxide, N,N-dimethylformamide, N,N-dimethylacetamide, dimethyl sulfone, tetramethylene sulfone, N-methylpyrrolidinone, and the like.

Bases useful in the practice of the invention include all bases strong enough to activate the oxazoline reactant, e.g., alkaline earth metal compounds such as calcium oxide, calcium hydride, calcium hydroxide, barium oxide, barium hydroxide, magnesium hydroxide, zinc hydroxide, etc. However, the base is preferably an alkali metal compound, e.g., an organoalkali metal compound, alkali metal hydride, alkali metal hydroxide, alkali metal oxide, alkali metal amide, or alkali metal alcoholate, such as butyllithium, phenyllithium, ethylsodium, amylsodium, butylpotassium, benzylpotassium, sodium dimsylate (i.e., the sodium salt of diethylsulfoxide), sodium hydride, potassium hydride, sodium hydroxide, potassium hydroxide, sodium oxide, potassium oxide, sodium amide, potassium amide, lithium diisopropylamide, sodium methoxide, potassium t-butoxide, the sodium salt of the monomethyl ether of ethylene glycol, sodium phenoxide, and the like. Ordinarily the use of potassium t-butoxide will be found most convenient and economical.

Use of an alkali metal compound as the base permits the alternatives of using the alkali metal compound alone or in conjunction with a phase transfer catalyst, such as a quarternary ammonium salt, ethylene glycol, or a suitable crown ether. When a phase transfer catalyst is employed (1) the alkali metal compound may be any of the alkali metal compounds generically or specifically indicated above, although the type of alkali metal compound being used determines the type of crown ether that is preferably utilized—lithium bases generally calling for the use of a 12-crown-4 ether, sodium bases generally calling for the use of a 15-crown-5 ether, and potassium bases generally calling for the use of an 18-crown-6 ether, and (2) the reaction medium may be any of the aprotic solvents mentioned above, or it may be an inert liquid hydrocarbon such as benzene, toluene, xylene, hexane, heptane, isooctane, or the like.

When an alkali metal hydride, especially a highly pure alkali metal hydride, is employed as the base, it is desirable to include a small amount of a transfer agent such as water, alcohol, or the like in the system. It is believed that the transfer agent activates the hydride by reacting therewith to form a small amount of the alkali metal hydroxide or alcoholate.

The fluoronitroaralkyloxazoline synthesis of the invention appears to occur by a nucleophilic substitution mechanism whereby the oxazoline undergoes a nucleophilic substitution on an unsubstituted ring carbon of the fluoronitroaromatic compound during which the alpha-substituent of the oxazoline functions as a leaving group. It is conducted in a substantially anhydrous reaction system, and accordingly, except when a small amount of water (which is itself consumed by reaction with the alkali metal hydride) is employed as a transfer agent as suggested above, the components of the reaction system should be brought together and maintained under a dry inert atmosphere. Thus, while it is possible to conduct the process in the presence of air, it is desirable to maintain the reaction system under an atmosphere of dry nitrogen or the like. Since the reaction itself is normally an exothermic reaction, with its initiation readily ascertainable by noting the exotherm produced, the reactants are ordinarily brought together at ambient temperatures, although the temperature may be raised or lowered to suit the needs of the occasion if desired.

The fluoronitroaromatic compound and alpha-substituted 2-alkyloxazoline may be used in amounts such as to provide a stoichiometric excess of either of the reactants or the stoichiometric amount of each. However, when a stoichiometric excess of the fluoronitroaromatic compound is employed, the quantity of product obtainable will be limited by the quantity of oxazoline used, so it is desirable to utilize a stoichiometric excess of the oxazoline. The amount of base employed is preferably such as to provide at least two molar equivalents of base per mol of fluoronitroaromatic compound, since the use of smaller amounts—although permitting the reaction to occur—makes the base the limiting reagent.

The mode of addition of the ingredient of the reaction system is not particularly critical. Accordingly, it is convenient to add the fluoronitroaromatic compound to a mixture of the other materials, add the base to a mixture of the other mterials, add the reactants to a mixture of the base and inert solvent, introduce all four ingredients simultaneously into the reaction zone, or the like. Since the reaction ordinarily proceeds very rapidly, long reaction times are not required. The reaction will usually be completed within a matter of minutes or a few hours at ambient temperatures.

When derivatives of the fluoronitroaralkyloxazolines are desired, they may be prepared by employing conventional techniques to convert to the desired derivatives the fluoronitroaralkyloxazolines made in accordance with the present invention. Thus, for example:

(1) 2-(3-fluoro-4-nitrobenzene)ethyl-4,4-dimethyloxazoline synthesized by the process of the invention may be hydrogenated to 2-(4-amino-3-fluorobenzene)ethyl-4,4-dimethyloxazoline, converted to a 2-(2-fluoro-4-biphenylyl)ethyl-4,4-dimethyloxazoline—preferably by a Gomberg-Bachmann reaction—and subsequently converted to 2-(2-fluoro-4-biphenylyl)propionic acid, and (2) 2-(3-fluoro-4-nitrobenzene)ethyl-4,4-dimethyloxazoline synthesized by the process of the invention may be converted to 2-(3-fluoro-4-nitrobenzene)propionic acid, hydrogenated to 2-(4-amino-3-fluorobenzene)propionic acid, and then coupled with benzene to form 2-(2-fluoro-4-biphenylyl)propionic acid, etc.

The particular conventional techniques used to convert the fluoronitroaralkyloxazolines into their various derivatives are not critical. It may sometimes be desirable to use certain particular techniques for the preparation of the derivatives, e.g., (a) the reduction and/or hydrolysis techniques taught in March, Advanced Organic Chemistry, McGraw-Hill, New York, 1977, pages 809–10, 1125–6, and the references cited therein; and (b) the Gomberg-Bachmann techniques taught in March, pages 653–4, and in Organic Reactions, Vol. 2, page 224 (1944); Journal of the American Chemical Society, Vol. 46, page 2339 (1924); Chemical Rev., Vol. 57, page 77 (1957); and Journal of the Chemical Society, Vol. D 1971, page 411, the disclosures of all of which are incorporated herein by reference. However, the overall processes for preparing the derivatives are simplified and made more efficient and economical by the present simplification of the synthesis of the fluoronitroaralkyloxazolines, regardless of the particular techniques used to convert them into their various derivatives.

As indicated above, the present invention is particularly advantageous in providing a readier and more economical route to the synthesis of flurbiprofen and other pharmaceuticals that can be prepared from fluoronitroaryloxazolines. Such products include, not only those mentioned above, but a variety of products, such as products disclosed in U.S. Pat. Nos. 3,641,040, 3,657,230, 3,767,805, 3,868,391, 3,936,467, 3,993,763, 3,997,669, 4,010,274, 4,118,504, 4,126,691, 4,163,788, and 4,239,901.

The following example is given to illustrate the invention and is not intended as a limitation thereof.

EXAMPLE

A suitable reaction vessel was charged with 10 ml of N,N-dimethylformamide (DMF) and cooled to $-10°$ C. Subsequently, 15 mmols of potassium t-butoxide were added, and then a solution of 7.1 mmols of 2-fluoronitrobenzene and 7.1 mmols of 2-(1-chloroethyl)-4,4-dimethyloxazoline in 2 ml of DMF. The reaction mixture was stirred at a temperature below 0° C. for an additional hour and then poured into water and adjusted to a pH of 8. Next the suspension was extracted with aliquots of ether, and the combined ether phases were washed with water to remove the DMF. The organic phase was dried over magnesium sulfate, filtered, and evaporated to provide about 1.9 g of a red-orange oil. GC/MS analyses showed the major product to be 2-[1-(3-fluoro-4-nitrophenyl)ethyl]-4,4-dimethyloxazoline.

I claim:

1. A 2-(aminofluorobenzenealkyl)oxazoline corresponding to the formula:

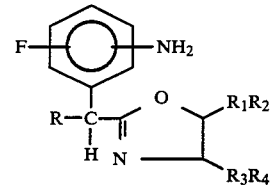

wherein R is halo or an alkyl group having not more than 10 carbons, and $R_1$, $R_2$, $R_3$, and $R_4$ are independently selected from hydrogen, methyl, and ethyl.

2. A 2-(4-amino-3-fluorobenzenealkyl)oxazoline of claim 1 wherein R is alkyl and $R_1$ and $R_2$ are hydrogen.

3. 2-[1-(4-amino-3-fluorobenzene)ethyl]-4,4-dimethyloxazoline.

* * * * *